United States Patent
Andrews

(10) Patent No.: US 9,642,753 B1
(45) Date of Patent: May 9, 2017

(54) APPARATUS AND METHOD FOR FORMING AND SECURING DISCRETE COMPONENTS TO MOVING WEBS

(71) Applicant: Curt G. Joa, Inc., Sheboygan Falls, WI (US)

(72) Inventor: Robert E. Andrews, Sheboygan, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 0 days.

(21) Appl. No.: 15/335,539

(22) Filed: Oct. 27, 2016

Related U.S. Application Data

(60) Provisional application No. 62/248,896, filed on Oct. 30, 2015.

(51) Int. Cl.
*A61F 13/00* (2006.01)
*A61F 13/10* (2006.01)
*A61F 13/15* (2006.01)

(52) U.S. Cl.
CPC .. *A61F 13/15804* (2013.01); *A61F 13/15699* (2013.01); *A61F 13/15723* (2013.01); *A61F 13/15764* (2013.01)

(58) Field of Classification Search
CPC .......... A61F 13/00; A61F 13/10; A61F 13/15; A61F 13/15; A61F 13/158; A61F 13/158; A61F 13/15804; A61F 13/156; A61F 13/156; A61F 13/1569; A61F 13/1569; A61F 13/15699; A61F 13/157; A61F 13/157; A61F 13/1572; A61F 13/1572; A61F 13/15723; A61F 13/1576; A61F 13/1576; A61F 13/15764
See application file for complete search history.

(56) References Cited

FOREIGN PATENT DOCUMENTS

| | | |
|---|---|---|
| EP | 2586411 B1 | 8/2014 |
| EP | 2691060 B1 | 1/2015 |

*Primary Examiner* — Michael N Orlando
*Assistant Examiner* — Matthew Hoover
(74) *Attorney, Agent, or Firm* — Ryan Kromholz & Manion, S.C.

(57) ABSTRACT

The present invention provides a method and apparatus for minimizing waste and improving quality and production in web processing operations in a high speed, small footprint environment. In particular, the invention is directed to aligning cuff webs, affixing no-waste ear webs to the cuff webs, and attaching the combination of back ears and cuff webs to a top sheet.

2 Claims, 4 Drawing Sheets

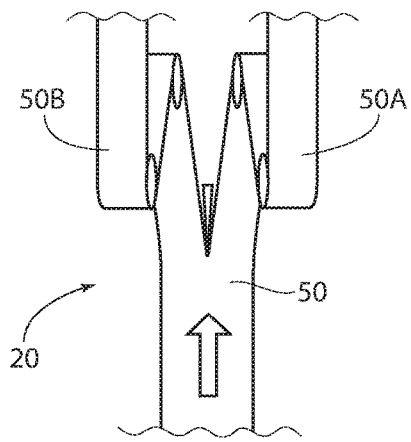
Fig. 3
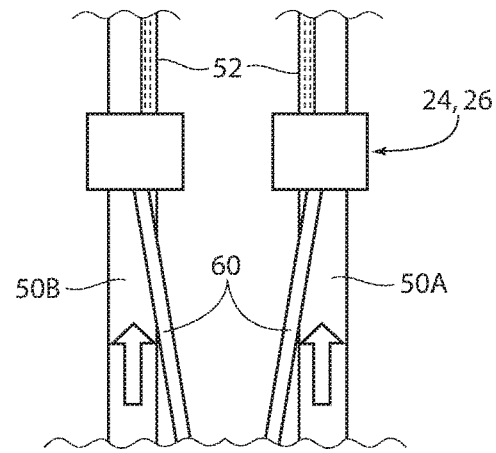
Fig. 4
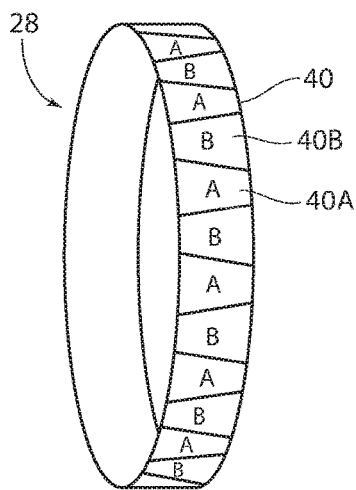
Fig. 5
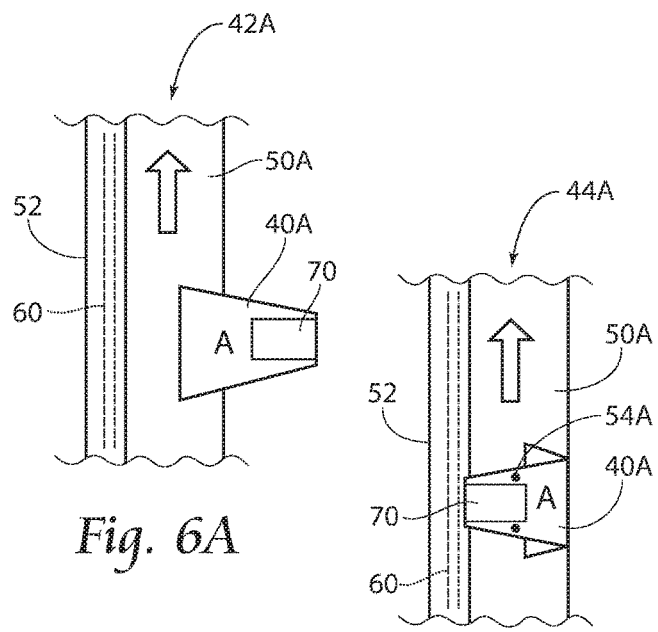
Fig. 6A
Fig. 6B

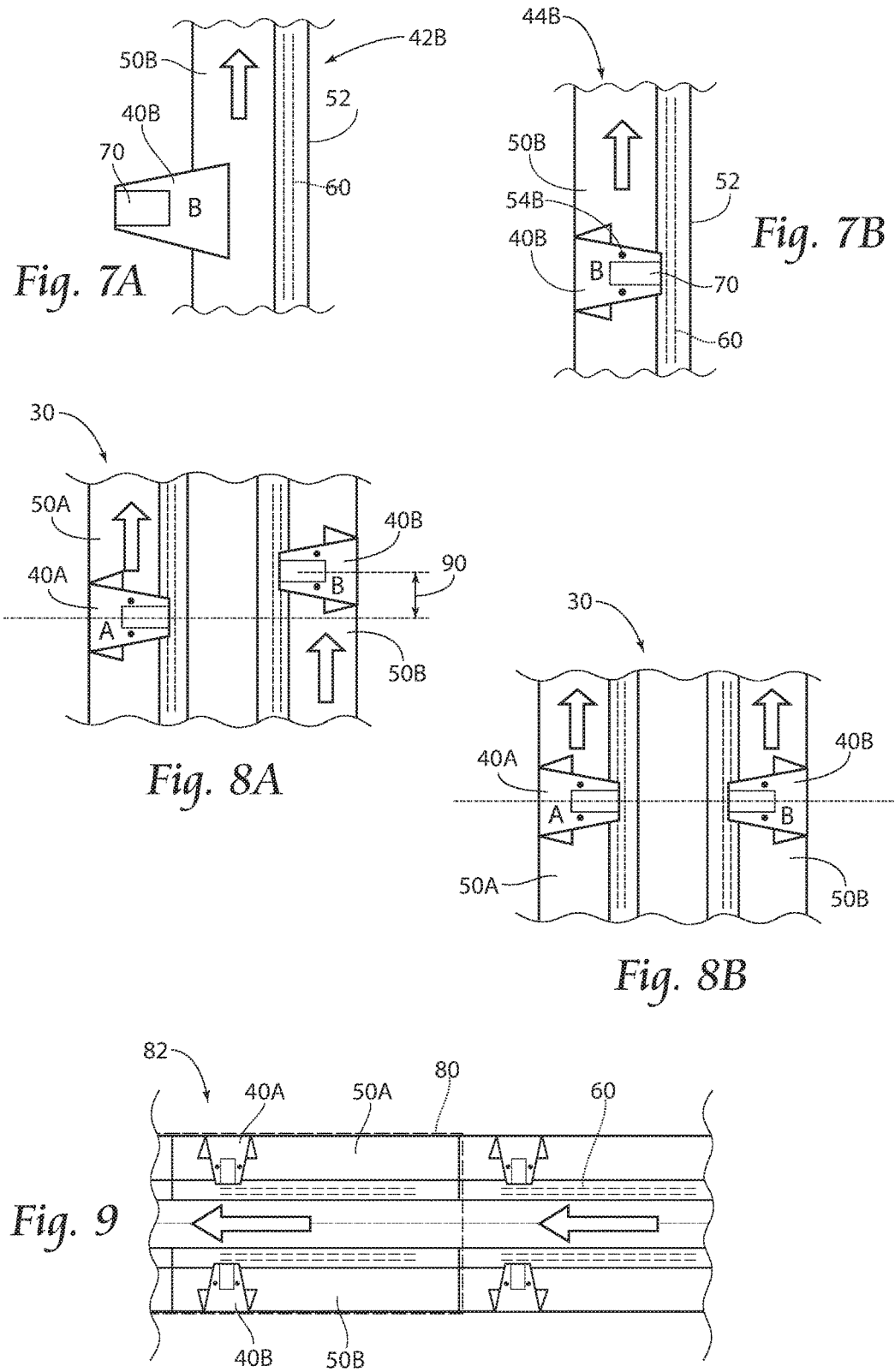

APPARATUS AND METHOD FOR FORMING AND SECURING DISCRETE COMPONENTS TO MOVING WEBS

RELATED APPLICATIONS

This application claims the benefit of U.S. Provisional Patent Application Ser. No. 62/248,396, filed 30 Oct. 2015.

BACKGROUND OF THE INVENTION

The invention disclosed herein relates to an apparatus and methods for forming disposable products such as diapers at very high speeds, while automatically scheduling certain aspects of production, including material loading, splicing, reloading. In particular, the present invention relates to affixing no-waste ear webs to cuff webs. While the description provided relates to diaper manufacturing, the apparatus and method are easily adaptable to other applications.

Generally, diapers comprise an absorbent insert or patch and a chassis, which, when the diaper is worn, supports the insert proximate a wearer's body. Additionally, diapers may include other various patches, such as tape tab patches, reusable fasteners and the like. The raw materials used in forming a representative insert are typically cellulose pulp, tissue paper, poly, nonwoven web, acquisition, and elastic, although application specific materials are sometimes utilized. Usually, most of the insert raw materials are provided in roll form, and unwound and applied in continuously fed fashion.

In the creation of a diaper, multiple roll-fed web processes are typically utilized. To create an absorbent insert, the cellulose pulp is unwound from the provided raw material roll and de-bonded by a pulp mill. Discrete pulp cores are created using a vacuum forming assembly and placed on a continuous tissue web. Optionally, super-absorbent powder may be added to the pulp core. The tissue web is wrapped around the pulp core. The wrapped core is debulked by proceeding through a calender unit, which at least partially compresses the core, thereby increasing its density and structural integrity. After debulking, the tissue-wrapped core is passed through a segregation or knife unit, where individual wrapped cores are cut. The cut cores are conveyed, at the proper pitch, or spacing, to a boundary compression unit.

While the insert cores are being formed, other insert components are being prepared to be presented to the boundary compression unit. For instance, the poly sheet is prepared to receive a cut core. Like the cellulose pulp, poly sheet material is usually provided in roll form. The poly sheet is fed through a splicer and accumulator, coated with an adhesive in a predetermined pattern, and then presented to the boundary compression unit. In addition to the poly sheet, which may form the bottom of the insert, a two-ply top sheet may also be formed in parallel to the core formation. Representative plies are an acquisition layer web material and a nonwoven web material, both of which are fed from material parent rolls, through a splicer and accumulator. The plies are coated with adhesive, adhered together, cut to size, and presented to the boundary compression unit. Therefore, at the boundary compression unit, three components are provided for assembly: the poly bottom sheet, the core, and the two-ply top sheet.

A representative boundary compression unit includes a profiled die roller and a smooth platen roller. When all three insert components are provided to the boundary compression unit, the nip of the rollers properly compresses the boundary of the insert. Thus, provided at the output of the boundary compression unit is a string of interconnected diaper inserts. The diaper inserts are then separated by an insert knife assembly and properly oriented, such as disclosed in co-pending U.S. Application No. 61/426,891, owned by the assignee of the present invention and incorporated herein by reference. At this point, the completed insert is ready for placement on a diaper chassis.

A representative diaper chassis comprises nonwoven web material and support structure. The diaper support structure is generally elastic and may include leg elastic, waistband elastic and belly band elastic. The support structure is usually sandwiched between layers of the nonwoven web material, which is fed from material rolls, through splicers and accumulators. The chassis may also be provided with several patches, besides the absorbent insert. Representative patches include adhesive tape tabs and resealable closures.

The process utilizes two main carrier webs; a nonwoven web which forms an inner liner web, and an outer web that forms an outwardly facing layer in the finished diaper. In a representative chassis process, the nonwoven web is slit at a slitter station by rotary knives along three lines, thereby forming four webs. One of the lines is on approximately the centerline of the web and the other two lines are parallel to and spaced a short distance from the centerline. The effect of such slitting is twofold; first, to separate the nonwoven web into two inner diaper liners. One liner will become the inside of the front of the diaper, and the second liner will become the inside of the back of that garment. Second, two separate, relatively narrow strips are formed that may be subsequently used to cover and entrap portions of the leg-hole elastics. The strips can be separated physically by an angularly disposed spreader roll and aligned laterally with their downstream target positions on the inner edges of the formed liners. This is also done with turn bars upon entrance to the process.

After the nonwoven web is slit, an adhesive is applied to the liners in a predetermined pattern in preparation to receive leg-hole elastic. The leg-hole elastic is applied to the liners and then covered with the narrow strips previously separated from the nonwoven web. Adhesive is applied to the outer web, which is then combined with the assembled inner webs having elastic thereon, thereby forming the diaper chassis. Next, after the elastic members have been sandwiched between the inner and outer webs, an adhesive is applied to the chassis. The chassis is now ready to receive an insert.

In diapers it is preferable to contain elastics around the leg region in a cuff to contain exudates for securely within the diaper. Typically, strands of elastic are held by a non-woven layer that is folded over itself and contains the elastics within the overlap of the non-woven material. The non-woven is typically folded by use of a plow system which captures the elastics within a pocket, which is then sealed to ensure that the elastics remain in the cuff.

Most products require some longitudinal folding. It can be combined with elastic strands to make a cuff. It can be used to overwrap a stiff edge to soften the feel of the product. It can also be used to convert the final product into a smaller form to improve the packaging.

To assemble the final diaper product, the insert must be combined with the chassis. The placement of the insert onto the chassis occurs on a placement drum or at a patch applicator. The inserts are provided to the chassis on the placement drum at a desired pitch or spacing. The generally flat chassis/insert combination is then folded so that the inner webs face each other, and the combination is trimmed.

A sealer bonds the webs at appropriate locations prior to individual diapers being cut from the folded and sealed webs.

As in many manufacturing operations, waste minimization is a goal in web processing applications. Indeed, due to the rate at which web processing machines run, even minimal waste can cause inefficiencies of scale. In present systems, waste materials are recycled. However, the act of harvesting recyclable materials from defective product is intensive.

Some diaper forming techniques are disclosed in co-pending U.S. application Ser. No. 12/925,033 which is incorporated herein by reference. As described therein, a process wherein a rotary knife or die, with one or more cutting edges, turns against and in coordination with a corresponding cylinder to create preferably trapezoidal ears. Ear material is slit into two lanes, one for a left side of a diaper and the other for a right side of a diaper. Fastening tapes are applied to both the right and the left ear webs. The ear material is then die cut with a nested pattern on a synchronized vacuum anvil.

The resulting discrete ear pieces however, due to the trapezoidal pattern of the ears, alternate between a correct orientation and an incorrect (reversed) orientation. The reversed ear is required to be rotated 180° into the correct orientation such that the ears and associated tape present a left ear and a right ear on the diaper.

To accomplish the reversal of the ear pattern, discrete ear pieces are picked up at the nested ear pitch by an ear turner assembly that will expand to a pitch large enough for ears to be unnested and allow clearance for every other ear to be rotated. The rotated ears are then unnested and into the correct orientation.

Two ear turner assemblies can be provided, to rotate every other ear applied to the right side of the product, and every other ear applied to the left side of the product. In this manner, for a single product, one of the two ears will have been rotated 180°.

Although the ear rotating apparatus provides an elegant and efficient solution for using no-waste ear webs, the industry could benefit from an alternative approach.

SUMMARY OF THE INVENTION

Provided are methods and an apparatus for minimizing waste and improving quality and production in web processing operations in a high speed, small footprint environment. In particular, the invention is directed to a cost effective and efficient solution for aligning and affixing no-waste ear webs to cuff webs.

DESCRIPTION OF THE DRAWINGS

FIG. 3 is a top plan view of a cuff spreader according to the present as indicated in FIGS. 1 and 2.

FIG. 4 is a top plan view of a LYCRA® fiber infeed and a cuff folder according to the present as indicated in FIG. 2.

FIG. 5 is a perspective view of a back ear die cut unit according to the present invention as indicated in FIGS. 1 and 2.

FIG. 6A is a top plan view of a drive side back ear attachment to a cuff web according to the present invention as indicated in FIGS. 1 and 2.

FIG. 6B is a top plan view of the drive side back ear shown in FIG. 6A folded as indicated in FIGS. 1 and 2.

FIG. 7A is a top plan view of an operator side back ear attachment to a cuff web according to the present invention as indicated in FIGS. 1 and 2.

FIG. 7B is a top plan view of the operator side back ear of FIG. 7A folded as indicated in FIGS. 1 and 2.

FIG. 8A is a top plan view of a potential drive side and operator side ear/cuff web alignment as indicated in FIG. 2.

FIG. 8B is a top plan view of a drive side and operator side ear/cuff web alignment as indicated in FIG. 2.

FIG. 9 is a top plan view of the ear/cuff webs and a top sheet combined according to the present invention as indicated in FIG. 2.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention.

Figure 1:
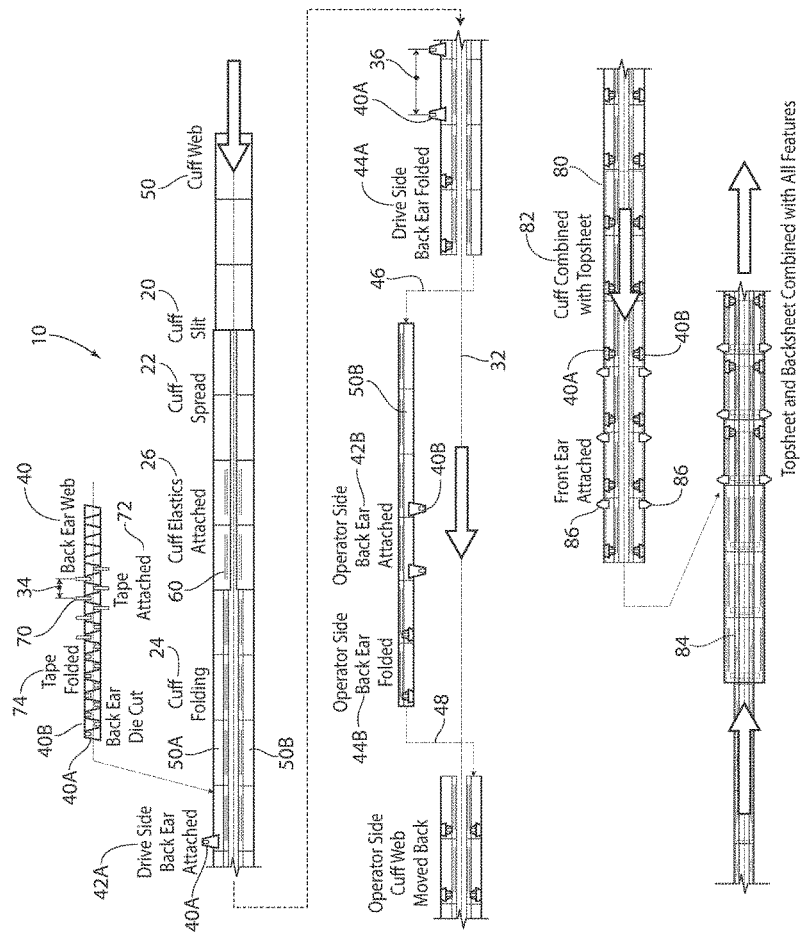
FIG. 1 is a flow diagram of a preferred embodiment of a process according the resent invention.

FIG. 1 shows a process 10 for attaching drive side and operator side back ears 40A, 40B to respective drive side and operator side cuff webs 50A, 50B according to the present invention. For clarity, arrows provided throughout the drawings are representative of machine direction.

Prior to reaching the process shown in FIG. 1, the cuff web 50 is preferably first fed through an accumulator (not shown) to provide a surplus of the cuff web 50 to enhance splicing of cuff web material without having to reduce the speed of the machinery. The cuff web 50 then goes through a dancer (not shown) to control the tension of the cuff web 50 and a web guide (not shown) to position the cuff web 50.

The cuff web 50 proceeds through a cuff slitter 20 to cut the cuff web 50 into a drive side cuff web 50A and an operator side cuff web 50B and through a cuff spreader 22 to spread the drive side cuff web 50A and the operator side cuff web 50B (see also FIG. 3).

Once separated, adhesive (not shown) is applied to each of the cuff webs 50A, 50B and LYCRA® fiber strands 60 are introduced from a LYCRA® fiber infeed 26 along a first side portion 52 of each cuff web 50A, 50B. Preferably, the LYCRA® fiber infeed 26 is positioned between the cuff webs 50A, 50B, wherein the first side portion 52 of each cuff web 50A, 50B is adjacent to the LYCRA® fiber infeed 26. A cuff folder 24 folds each respective first side portion 52 to enclose the LYCRA® fiber strands 60 (see also FIG. 4).

Preferably, concurrently with the process of forming the cuff webs 50A, 50B disclosed above, a process of forming a drive side back ear 40A and an operator side back ear 40B is provided. The back ear web 40 is preferably configured in a no-waste orientation as shown in FIGS. 1 and 5, wherein, the back ears 40A, 40B are provided in an alternating trapezoidal pattern formed by a back ear die cut unit 28.

Figure 2:
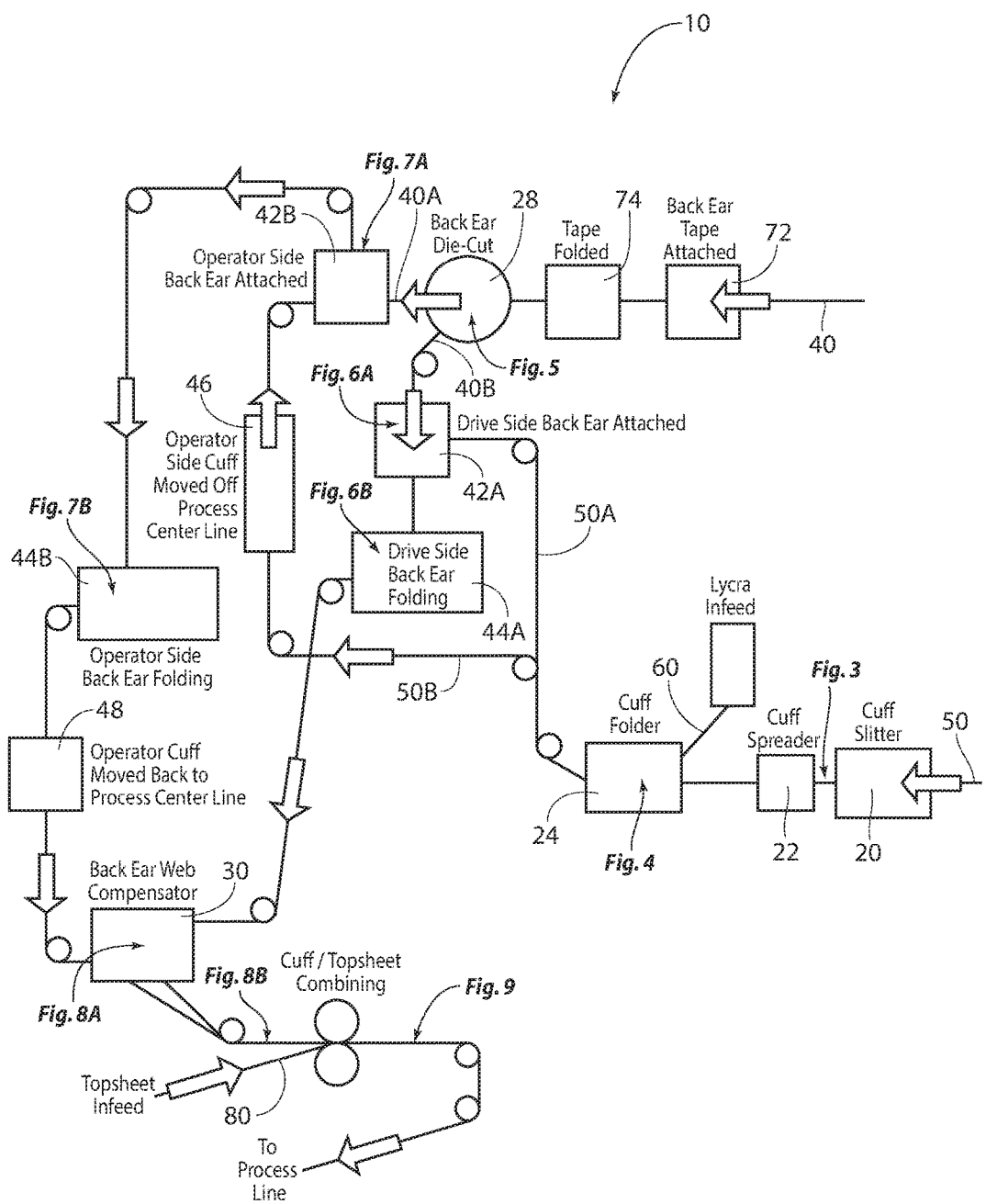
FIG. 2 is a schematic of an apparatus configured to perform the process shown in FIG. 1.

Prior to being attached to the drive side and operator side cuff webs 50A, 50B, tape 70 is attached 72 to each back ear 40A, 40B and folded 74 as shown in FIGS. 1 and 2. The back ears 40A, 40B are preferably formed into the trapezoidal no-waste shape on a trapezoidal die unit 28. The back ears 40A, 40B are then processed through a combination of transfer rolls (not shown) to a bonding roll (not shown) and finally to the respective cuff web 50A, 50B. In one embodiment, as taught in U.S. Pat. No. 9,433,538 incorporated herein by reference, every back ear 40A is gathered and sent to the operator side, and every back ear 40B is gathered and sent to the drive side. This can be done as shown in FIGS. 110-112 of U.S. Pat. No. 9,433,538.

The distance between the respective ears 40A, 40B from a first ear distance 34 to a second ear distance 36 is also shown in FIG. 1. The second ear distance 36 being greater than the first ear distance 36.

Although not specifically shown in the Figures, it is preferable that the back ear die cut unit 28 be physically located above the top edge of the drive side cuff web 50A.

Looking now to FIGS. 6A and 6B, and as provided in FIGS. 1 and 2, the drive side back ear 40A is shown attached to the drive side cuff web 50A. The attachment of the drive side back ear 40A at this point is preferably carried out through a mechanical or pressure tack bonding process.

The drive side cuff web 50A is generally pre-aligned and ready to receive the drive side back ear 40A from the back ear die cut unit 28. This placement eliminates the need to have the drive side cuff web 50A shifted and realigned into position with the drive side back ear 40A and reduces the number of steps required to attach the back ears 40A, 40B to the cuff webs 50A, 50B.

Preferably, after the drive side back ear 40A is attached 42A to the drive side cuff web 50A, the drive side back ear 40A is folded 44A and tacked 54A as shown in FIG. 6B. The tacking 54A may be accomplished by any means now known or later developed. Non-limiting examples include tacking with adhesive, ultrasonic bonding, or applied pressure.

FIGS. 7A and 7B, and as provided in FIGS. 1 and 2, show the operator side back ear 40B being attached to the operator side cuff web 50B. Because the back ear die cut unit 28 is positioned in-line with the drive side cuff web 50A and the operator side back ears 40B are oriented in the opposite direction as the drive side back ears 40A, the operator side cuff web 50B must be realigned in a first shift 46 and oriented in a manner to properly receive the operator side back ears 40B. The first shift 46 is preferably carried out with at least a turn bar assembly (not shown).

As shown in FIGS. 1 and 2, the first shift 46 requires the operator side cuff web 50B to be moved off of the process center line 32 to receive the operator side back ear 40B. The attachment 42B of the operator side back ear 40B at this point is preferably carried out through a mechanical or pressure tack bonding process and occurs approximately 90° from the attachment of the drive side back ear 40A. Similar to the drive side back ear 40A, the operator side back ear 40B is folded 44B and tacked 54B after being attached 42B to the operator side cuff web 50B.

The operator side cuff web 50B is then realigned in a second shift 48 to be spaced a predetermined distance from the drive side cuff web 50A, with the process center line 32 between and equidistant to each cuff web 50A, 50B. The second shift 48 is preferably carried out with at least a turn bar assembly (not shown). The two cuff webs 50A, 50B, with attached back ears 40A, 40B, are thereby positioned to be attached 82 (FIG. 1) to a topsheet 80.

Due to the repositioning and shifting of the operator side cuff web 50B, more of the operator side cuff web 50B travels through the process 10 prior to receiving the operator side back ear 40B than does the drive side cuff web 50A prior to receiving the drive side back ear 40A. The operator side cuff web 50B will always be behind the drive side cuff web 50A by the difference in distance the operator side cuff web 50B travels through the process 10. Thus, portions of the cuff web 50 that are adjacent prior to undergoing the process 10 are never reunited with same adjacent portion by the time they are attached to the topsheet 80.

In some instances, because of the different paths taken by the drive side cuff web 50A and the operator side cuff web 50B through the process, the back ears 40A, 40B, attached to the respective drive side cuff web 50A and the operator side cuff web 50B, may be out of alignment, defining a gap 90 (FIG. 8A). Therefore, prior to attachment to the topsheet 80, the drive side and operator side cuff webs 50A, 50B are preferably processed through a back ear web compensator 30 which will adjust and compensate any difference between the drive side and operator side cuff webs 50A, 50B to align their respective back ears 40A, 40B, if needed.

After the combination of the topsheet 80, the drive side cuff web 50A with attached drive side back ear 40A, and the operator side cuff web 50B with attached operator side back ear 40B is completed, the combination proceeds down the process line to be combined with other elements of the garment, including, but not limited to, an absorbent core 84 and front ears 86.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been descried, the details may be changed without departing from the invention, which is defined by the claims.

I claim:

1. A method of producing a disposable product, the method comprising:
    providing an operator side cuff web comprising elastics carried by a folded over portion of said operator side cuff web at an operator cuff web first edge;
    providing a drive side cuff web comprising elastics carried, by a folded over portion of said drive side cuff web at a drive side cuff web first edge;
    severing an ear web into drive side and operator side ear configurations;
    coupling said operator side ear configuration to said operator side cuff web;
    coupling said drive side ear configuration to said drive side cuff web;
    providing a topsheet web comprising a drive side and an operator side;
    coupling said operator side cuff web to said operator side of said topsheet web;
    coupling said drive side cuff web to said drive side of said topsheet web.

2. A method according to claim 1, wherein said operator side cuff web is positioned away from a process center line prior to the step of coupling said operator side ear configuration to said operator side cuff web, and wherein said operator side cuff web is positioned at said process center line following the step of coupling said operator side ear configuration to said operator side cuff web.

* * * * *